United States Patent [19]

Mauthner

[11] Patent Number: 4,983,375

[45] Date of Patent: Jan. 8, 1991

[54] HEMATOLOGICAL STAIN SYSTEM

[75] Inventor: Thomas Mauthner, Livonia, Mich.

[73] Assignee: Cambridge Diagnostic Products, Inc., Ft. Lauderdale, Fla.

[21] Appl. No.: 425,126

[22] Filed: Oct. 23, 1989

[51] Int. Cl.$^5$ .......................... G01N 1/00; G01N 1/30
[52] U.S. Cl. ......................................................... 424/3
[58] Field of Search ............................................. 424/3

[56] References Cited

U.S. PATENT DOCUMENTS 3,670,072  6/1972  Mauthner ................................ 424/3
3,678,151  7/1972  Horonick et al. ....................... 424/3

Primary Examiner—Douglas W. Robinson
Assistant Examiner—Kevin Weddington
Attorney, Agent, or Firm—Krass & Young

[57] ABSTRACT

A hematological stain includes Wright's stain powder together with a thiazole dye and a pH control agent which is a neutral or near neutral salt. The stain may further include a surfactant as well as buffers and antioxidants.

19 Claims, No Drawings

HEMATOLOGICAL STAIN SYSTEM

FIELD OF THE INVENTION

This invention relates to hematological staining systems in general. More specifically, the present invention relates to improved Wright's stain solutions.

BACKGROUND OF THE INVENTION

The use of stains is very important in the investigation of biological tissues and is of particular importance in hematology. By the use of appropriate stains, the various components of blood, such as platelets, cells and structures thereof may be selectively visualized, facilitating microscopic inspection of the blood sample and the identification of deviant morphologies and/or disease causing organisms. There are a variety of stains utilized in hematology. These stains are typically organic dyes having differential affinities for various cells and cell structures. One of the most commonly employed stains is what is referred to as Wright's stain. This stain, also called RG stain in Europe is a mixture of dyes prepared by the steps of oxidizing methylene blue and precipitating the mixture with tetrabromofluorescein. The preparation of this mixture of dyes was first described by J. H. Wright in the Journal of Medical Research, Volume 7, p. 138, 1902. Wright's stain is typically provided in the form of a prepared powder referred to as "Wright's stain powder". This is a staple item of commerce available from a variety of suppliers including the Aldrich Chemical Corporation of Milwaukee, Wis.

Commercially available Wright's stain is a complex mixture of many different dyes some of which are active and some of which are inactive, although it is generally agreed that the most important components are the azure A and azure B dyes. It has generally been found that the best Wright's stain usually has a first absorption maximum between 650–656 nm and a separate Eosin absorption peak around 517 nm although these peaks may differ significantly from batch to batch of dyes without significantly impairing stain function. It should be clear from the foregoing that the exact composition of a batch of Wright's stain powder is variable and is usually not precisely determined. For this reason, the term "Wright's stain powder" as utilized herein is generally meant to refer to methylene blue derived stain mixtures as are well-known and available to those of skill in the art and as such is a generic term and not restricted to any one specific dye mixture.

Although Wright's stain has been known for some time, its use is not without problems. It has previously been found that Wright's stain suffers from problems of stability, both of the prepared solution and the sample stained thereby. U.S. Pat. No. 3,670,072, the disclosure of which is incorporated herein by reference, recognizes these problems of stability and provides for an improved stain system incorporating Wright's stain powder together with buffers and anti-oxidant fixatives. The invention of the '072 patent provides for a fast acting and permanent staining system.

Despite these advances, there are still problems associated with Wright's stain materials. For example, it has been found that in many instances the granulation of stained white blood cells is indistinct. This effect correlates with particular batches of Wright's stain powder and also appears to be related to the pH of the blood samples. Incorporation of the afore-mentioned buffers does not fully address problems of indistinct granulation and further investigation suggests that the pH of the dried blood samples may affect the differentiation of the granulation. Another problem with stain materials of this type is that the color imparted to the blood cells is frequently too blue thereby preventing resolution of fine detail and differentiation of cell structures. It is believed that this problem also relates inter alia to inconsistencies in the commercially available Wright's stain powder. These problems are particularly important now that computerized interpretation of blood smears is coming into use. The use of such automated methods exacerbates the need for quicker and more uniform staining of blood smears. Toward that end, there is a need for improved wetting agents.

Yet another problem which occurs in connection with the use of various stain materials is the presence of artifacts therein. These artifacts comprise particulate contaminants in the stain solution, which may be undissolved dye particles, trace contaminants and the like. These artifacts can interfere with interpretation of test results and are particularly troublesome in connection with automated evaluation systems.

It will thus be appreciated that there is a need for a Wright's stain system which enhances the structure of the granulation of white blood cells and improves the overall differentiation of cell structure by eliminating the effects of any "blue shift". It is further desired that these Wright's stain systems include a low number of artifacts and uniformly and rapidly wet and stain blood samples. The present invention provides an improved Wright's stain system which: greatly enhances the details of cell granulation, provides a color balance which maximizes differentiation of cell structures, is low in artifacts and rapidly and consistently stains a variety of blood samples. These and other advantages of the present invention will be readily apparent from the discussion and examples which follow.

BRIEF DESCRIPTION OF THE INVENTION

There is disclosed herein an improved hematological stain comprising Wright's stain powder and a thiazole dye. The thiazole dye may be selected from the group consisting essentially of: thiazole yellow G, thioflavin TCM, primulin, thioflavin S and combinations thereof. In general, the Wright's stain powder and thiazole dye are present in an approximately 5:1 to 10:1 weight ratio respectively. The stain may further include a polar, organic solvent and a buffer.

In a further embodiment, a Wright's stain solution is saturated with a neutral or near-neutral salt of a strong acid and a strong base. The stain solution may further include a flocculating agent and/or a surfactant and/or an antioxidant.

DETAILED DESCRIPTION OF THE INVENTION

When utilizing heretofore available Wright's stain compositions, it was found that white blood cells stained thereby often manifest an undesirable definition of the granulation and the overall coloration of the stained blood cells was too blue. These problems appear to arise when the pH of the stained blood smear is too high; however, buffering the stain to a pH of between 6.4 and 6.5 did not eliminate these problems. Further lowering of the pH did not improve the results but lead to bleaching of the red cells and generation of inconsistent staining colors. It was also noted that these problems were more severe for some batches of Wright's stain powder than for others.

In accord with the principles of the present invention, it was found that the pH of the stained, dried blood slide as well as the pH of the staining solution must be controlled in order to optimize staining of the granules. Experiments were carried out wherein stained blood smears were extracted using a 50/50 methyl alcohol-deionized water solution having a pH of approximately 6.95–7.00. While the stain was buffered to a pH of approximately 6.4–6.5 it was found that nearly one out of five of the dried, stained slides had a pH considerably higher than that of the staining solution. Out of a sample of 100 slides, it was found that 18 had an elevated pH and this pH averaged 6.76 (with a range of 6.68–6.90). The granules of the white blood cells of the high pH slides had a mushy appearance. As noted above, simply lowering the pH by changing the buffer composition did not cure this problem.

It has been found that the addition of a strong electrolyte composed of a neutral or nearly neutral salt of a strong acid and a strong base greatly stabilizes the pH of the slide and makes the granulation quite distinctive. The term "neutral or nearly neutral" refers to a salt which has a pH of approximately seven in aqueous solution. It has been found that there are a great variety of neutral or nearly neutral salts which may be employed in the practice of the present invention, such salts generally include, by way of illustration and not limitation, the halide nitrate, nitrate, sulfate and sulfite salts of Group I and Group II metals. Among some of the most preferred salts are potassium and lithium chloride. These salts are sparingly soluble in methyl alcohol and glycerine and are compatible with the buffer material as well as the Wright's stain dyes. Inclusion in the stain composition of a sufficient amount of such salts to saturate the solution therewith, eliminates the occasional fluctuation of the pH of dried blood smears developed upon staining and enhances the detail of the white blood cell granules.

In addition to causing the problem of granule differentiation, heretofore available Wright stain compositions frequently yield a poor color distinction of the variously stained components of the blood. It has been found that Wright's stain powder, particularly stain powder presently being produced, has a tendency to shift all colors toward the blue end of the spectrum, even when prepared at an optimum pH. This blue shift makes the different shades of the variously stained cell components less distinguishable. Spectroscopic investigations of Wright's stain powder indicates a variation in the spectral absorption of material from batch to batch. Typically, some powders have a relatively narrow absorption maxima at 652–656 nm while others have a broader maximum at 650–670 nm or even at 652–680 nm. Various other batches had small, additional peaks between 628–635 nm. It has been noted that Wright's stain powder with spectra manifesting relatively wide and strong absorption peaks contributes most strongly to the blue shift effect, particularly when the material has significant absorption at wave lengths greater than 656 nm.

It has been found in accord with the principles of the present invention that by the addition of a relatively small amount of a thiazole dye., the effect of the blue shift is overcome. Stains including dyes of this class have been found to be selectively absorbed by the erythrocytes and eosinophil leukocyte granules giving them a bright red color instead of the grayish pink tone obtained with prior art stains. Furthermore, the inclusion of thiazole dye in the stain formulation improves the shades of all lilac and purple colored granules and particles. The amount of thiazole dye is typically fairly low and in general the ratio of Wright's stain powder to thiazole dye is within the approximate range of 5:1 to 10:1 although the precise ratio will depend upon the absorption spectrum of the particular thiazole dye employed and in some instances may fall outside of this range.

There are a great number of dyes in the thiazole class and all of such dyes have significant utility in the practice of the present invention. In general, these dyes are characterized by the inclusion of a thiazole group, which is a five membered ring having the general structure of S—C=N—C=C—; the thiazole ring is usually fused with an aromatic ring through the C=C bond and the indamine group is usually the chromophore in these types of dyes. Among some of the thiazole dyes having particular utility in the present invention are: thioflavin TCN (C.I. 49005); thiazole yellow G (C.I. 19540); primulin (C.I. 49000); thioflavin S (C.I. 49010). Thiazole yellow G is one particularly preferred thiazole dye useful in the present invention. It is soluble in both water and alcohol and has an absorption maximum around 400 nm. It provides a close to optimum color equilibrium in stained blood smears and repeatable and reliable staining from batch to batch. There are a great variety of thiazole dyes known in the art; additionally, one of skill in the art could readily design and synthesize a plethora of other thiazole dyes as well as thiazole-type dyes, variants and analogs of which can have utility in the present invention.

Many laboratories are now using at least partially automated staining equipment wherein a slide having a blood smear flows through, or is otherwise exposed to, a staining solution. Contact time of the sample and stain is usually less than 30 seconds. Accordingly, it is necessary to have a staining solution which can repeatably, uniformly and reliably stain a blood sample in this time. Heretofore, various wetting agents, or surfactants (the terms being used interchangeably) have been added to stain solutions in an attempt to facilitate contact of the solution with the blood sample; however, it has been found that conventional wetting agents either had no effect, or a very adverse effect on the blood film. For example, it has been found that in some instances even very small amounts of wetting agent can alter the consistency of the blood smear.

It has been found in accord with the principles of the present invention that particular block copolymers have sufficient wetting ability to reduce the surface viscosity of the blood smear but are not reactive to alter the blood film. These materials reduce surface viscosity at the dye-blood interface facilitating absorption of the dyes onto the blood particulates with greater speed and intensity. A general class of such copolymers comprise variants of the ethylene oxide-propylene oxide copolymer system prepared by a method wherein ethylene oxide is added onto ethylene glycol to prepare a hydrophile which is then reacted with propylene oxide to obtain a hydrophobic block on the outside of the molecule. In general, these polymers are represented as being comprised of a stack of: a propylene oxide block, an ethylene oxide block and a propylene oxide block.

Block copolymers of this type having utility in the present invention are marketed by the BASF Corporation under the registered trademark "Pluronic R". In particular, it has been found that the Pluronic® R Series compounds 17-R1, 25-R1 and 17-R2 consistently act to improve the speed and absorption of stain and enhance intensity of the colors provided thereby. The Pluronic® R surfactants are differentiated from other block copolymer surfactants in that the molecules thereof are terminated by hydrophobic blocks. These surfactants are further characterized by having secondary hydroxyl groups terminating the molecules thereof and as such are differentiated from other surfactants of this type having terminal, primary hydroxyl groups. In general, the surfactants comprise approximately 0.2–0.8% by weight of the stain composition.

Stain compositions typically include a number of artifacts therein. These artifacts may comprise small crystals of the component materials of the stain, dust particles, mineral particles and like contaminants. It has been found that the incorporation of relatively small amounts of the foregoing surfactants in stain compositions facilitates removal of these artifacts from stained blood smears by rinsing.

Further problems of artifact formation occur as a result of aging, when a prepared stain solution undergoes undesirable chemical changes, usually oxidation. The various materials in Wright's stain are easily oxidized and, if methanol is present as a solvent, it may also oxidize, resulting in the formation of formic acid and subsequent precipitation of the dye. Addition of a small amount of a reducing agent, such as thiourea stabilizes the solution to oxidation, further preventing precipitation. Despite these precautions it has been found that at very high magnifications (1,500× or more) there are still submicron size particulates present in the stain solution. These particles are too small to be efficiently removed by filtration; however, it has been found in accord with the principles of the present invention that by the inclusion of a relatively small amount of a flocculating agent, aggregation of the small particles is effected and they may be removed by filtration. Certain metal salts, such as the salts of calcium, aluminum and magnesium have good flocculating properties and such salts may be added to the stain formulation of the present invention to facilitate removal of very small particles. It is generally preferred that the acetate salts be employed insofar as the acetate ion will not interfere with the buffers which are preferably employed in the present invention.

The stain solutions of the present invention are typically prepared in a polar solvent base, which solvent generally includes an alcohol such as methanol, ethanol, propanol, isopropanol, ethylene glycol, propylene glycol, glycerine and combinations thereof. The composition also preferably includes a buffer operative to maintain the pH of the mixture within a selected range, typically 4.7–8.0 and preferably 6.0–6.5 as is disclosed in patent '072. There are a great variety of buffer systems which may be employed in a stain of this type. One particular buffer system is comprised of sodium acetate and citric acid.

In general, stain compositions made in accord with the present invention will include by weight, approximately: 0.3–0.5% Wright's stain powder; .0.03–0.1% of a thiazole dye; approximately 0.2–0.5% of a neutral or near neutral salt of a strong acid and a strong base and 0.2–1% of a block copolymer surfactant of the Pluronic® R type. The stain is dissolved in a polar solvent, typically an alcohol-glycerine mixture and further includes buffers, anti-oxidants and flocculating agents as noted hereinabove.

One particular group of compositions having utility in the present invention comprise by weight:

| | |
|---|---|
| Methyl alcohol | 82.0–90.0% |
| Glycerine (99.7%) | 8.0–15.0% |
| Sodium Acetate | 0.40–0.80% |
| Citric Acid | 0.03–0.07% |
| Thiourea | 0.03–0.07% |
| Wright's stain powder | 0.30–0.50% |
| Thiazole yellow G | 0.03–0.06% |
| Lithium chloride | 0.20–0.40% |
| Magnesium or calcium acetate | 0.001–0.01% |
| Pluronic ® 17 R1 | 0.20–0.80% |

One specific embodiment of stain prepared in accord with the foregoing comprised by weight: 88.51% methyl alcohol; 9.70% glycerine; 0.515% sodium acetate; 0.047% citric acid; 0.047% thiourea; 0.40% Wright's stain powder; 0.043% thiazole yellow G; 0.256% lithium chloride; 0.003% magnesium acetate and 0.47% Pluronic® 17 R1.

One of skill in the general chemical arts and more particularly the art of formulating stain compositions knows that the optimum amount of ingredients for a given formulation may deviate from the aforementioned ranges, depending upon the purity of chemicals, et cetera. Typically, the optimum pH value of the formulation is between 6.20 and 6.40, with the best value being 6.28–6.32. To achieve this pH range it may be necessary to increase or decrease the amounts of sodium acetate, citric acid and lithium chloride. Due to the fact that the Wright's stain may vary from bottle to bottle it may also be necessary to vary the amount of thiazole dye.

In a typical process for the manufacture of the stain composition of the present invention, the solvents, buffer, thiourea, Wright's stain, thiazole dye and salt are gently agitated in a jacketed stainless steel vessel which is vented through a desiccator containing silica gel, calcium chloride or like material. Temperature of the mixture is raised from ambient to approximately 85°–95° F. and agitation maintained for 6–8 hours. The vessel is cooled to 62°–66° F. by running cold water through the jacket and intermittent agitation is provided. The mixture is allowed to stand for one hour and is filtered through a medium of approximately 1–5 micron. After filtration the flocculating agent (calcium acetate or magnesium acetate) and the surfactant are added. The mixture is stirred for two hours and allowed to stand for 2–4 hours and is again filtered.

A solution was prepared in accord with the foregoing and approximately 400 slides of blood smears, embodying 20 different types of blood were stained. It was found that the identification of both normal and abnormal cells was much easier than with previously available stain solutions. It was noted that red blood cells presented a very uniform pink coloration with a slight yellow/brown cast. Platelets stained dark purple with even darker centers while white blood cells were clear and distinct with an excellent range of contrast. The eosinophilic granules stained bright red to orange/red; thrombocytes stained lilac; lymphocytes stained royal blue; cytoplasm stained very light blue to pink with medium purple granules. Monocytes stained light blue with a lilac nucleus and basophils stained dark purple.

In a second experiment, three batches of Wright's stain powder known to give inconsistent results in connection with prior art formulations were utilized to prepare three separate batches of stain solution in accord with the foregoing general procedure. The sodium acetate-citric acid buffer comprised 0.5% by weight of the solution and the lithium chloride electrolyte comprised 0.2% of the solution and the remaining ingredients were in the aforementioned amounts. The pH of the three solutions (when mixed 50–50 with deionized water) ranged from 6.28 to 6.32. Two hundred slides of blood samples were prepared with each of the stain mixtures, utilizing 10 each of 20 different blood samples. All of the slides showed distinct granulation of white blood cells with colors ranging from lilac to purple. The dried, stained smears were extracted with a 50:50 mixture of methanol-deionized water as in the previous example and it was found that the pH of the extracts ranged from 6.36–6.42 and no upward deviation of pH was found.

It will thus be seen that the present invention provides for an improved Wright's type stain solution which stabilizes the pH of the dried blood smears and hence provides for a more distinct visualization of the granulation of white blood cells; the invention further provides for an increased differentiation between the various blood components and further eliminates the presence of non-cellular artifacts in the stained sample.

As detailed herein, the present invention employs a near-neutral salt of a strong acid and a strong base as a pH control agent, in addition to the formerly employed buffer solution. The stain of the present invention includes a thiazole-type dye to eliminate blue shift and may also include block copolymer surfactants and/or wetting agents. It will be appreciated that there are many compositions which may be prepared in accord with the principles of the present invention. One of skill in the art could readily substitute any one of a variety of near neutral salts, thiazole dyes, thiazole-type dyes and copolymers for the reagents disclosed herein while keeping within the scope of the present invention. Accordingly, it is to be understood that the foregoing discussion and examples are merely illustrative of particular principles of the present invention and are not limitations upon the practice thereof. It is the following claims, including all equivalents, which define the scope of the invention.

I claim:

1. An improved hematological stain comprising Wright's stain powder and a thiazole dye.

2. A stain as in claim 1, wherein said thiazole dye is selected from the group consisting essentially of thiazole yellow, thioflavin TCN, primulin, thioflavin S and combinations thereof.

3. A stain as in claim 1, wherein said Wright's stain powder and thiazole dye are present in an approximately 5:1 to 10:1 weight ratio respectively.

4. A stain as in claim 1, further including a buffer operative to maintain the pH of said stain at approximately 6.2–6.4.

5. A stain as in claim 1 further including a flocculating agent which comprises a salt of a member chosen from the group consisting essentially of calcium, aluminum, magnesium and combinations thereof.

6. A stain as in claim 1, further including a surfactant of the type comprising block polymer of alternating hydrophobic blocks and hydrophilic blocks wherein the molecule is terminated by hydrophobic blocks.

7. A stain as in claim 1, further including a polar, organic solvent.

8. A stain as in claim 7, wherein said solvent is selected from the group consisting essentially of methanol, ethanol, propanol, isopropanol, ethylene glycol, propylene glycol, glycerine and combinations thereof.

9. A stain as in claim 7, wherein said solvent is saturated with a neutral or near neutral salt of a strong acid and a strong base.

10. An improved hematological stain comprising at least one organic dye, a polar organic solvent, a buffer operative to maintain said stain at a pH of approximately 6.0–7.0 and a neutral or near neutral salt of a strong acid and a strong base in an amount sufficient to saturate said solvent with respect thereto.

11. A stain as in claim 10, wherein said solvent is selected from the group consisting essentially of methanol, ethanol, propanol, isopropanol, ethylene glycol, propylene glycol, glycerine and combinations thereof.

12. A stain as in claim 10, wherein said salt is a Group I or Group II metal halide.

13. A stain as in claim 12, wherein said salt is selected from the group consisting essentially of potassium chloride and lithium chloride.

14. An improved hematological stain solution comprising by weight:
80–90% of a C1–C3 monohydric alcohol;
5–20% of a polyhydric alcohol;
0.2–1% of a buffer operative to maintain the pH of the stain at approximately 6–7;
0.01–0.1% of an anti-oxidant;
0.2–0.8% Wright's stain powder;
0.01–0.1% of a thiazole dye; and
an alkali metal halide in an amount sufficient to saturate said solution.

15. A stain as in claim 14, further including 0.001–0.01% by weight of a flocculating agent which comprises a salt of a member chosen from the group consisting essentially of calcium, aluminum, magnesium and combinations thereof.

16. A stain as in claim 14, further including a surfactant of the type comprising block polymer of alternating hydrophobic blocks and hydrophilic blocks wherein the molecule is terminated by hydrophobic blocks.

17. A stain as in claim 14, wherein said buffer includes sodium acetate and citric acid and wherein said sodium acetate comprises, by weight, approximately 0.25–1% of said stain and said citric acid comprises, by weight, approprimately 0.01–0.1% of said stain.

18. A stain as in claim 14, wherein said anti-oxidant comprises thiourea.

19. An improved hematological stain solution comprising by weight:
82–90% methanol;
8–15% glycerine;
0.4–0.8% sodium acetate;
0.03–0.07% citric acid;
0.03–0.07% thiourea;
0.3–0.5% Wright's stain powder;
0.03–0.06% thiazole yellow G dye;
0.2–0.4% lithium chloride;
0.2–0.8% of a block copolymer wetting agent; and
a flocculating agent.

* * * * *